(12) United States Patent
Von Rosenberg et al.

(10) Patent No.: US 11,633,142 B2
(45) Date of Patent: Apr. 25, 2023

(54) ELECTROCARDIOGRAM APPARATUS AND METHOD

(71) Applicant: IMPERIAL COLLEGE OF SCIENCE, TECHNOLOGY AND MEDICINE, London (GB)

(72) Inventors: Wilhelm Von Rosenberg, Leonberg (DE); Valentin Goverdovsky, Amsterdam (NL); Theerasak Chanwimalueang, Bangkok (TH); Danilo Mandic, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 244 days.

(21) Appl. No.: 16/757,253

(22) PCT Filed: Oct. 18, 2018

(86) PCT No.: PCT/GB2018/053021
§ 371 (c)(1),
(2) Date: Apr. 17, 2020

(87) PCT Pub. No.: WO2019/077363
PCT Pub. Date: Apr. 25, 2019

(65) Prior Publication Data
US 2021/0093216 A1    Apr. 1, 2021

(30) Foreign Application Priority Data

Oct. 18, 2017 (GB) .................................... 1717092

(51) Int. Cl.
*A61B 5/00*    (2006.01)
*A61B 5/352*   (2021.01)
(Continued)

(52) U.S. Cl.
CPC .......... *A61B 5/352* (2021.01); *A61B 5/02007* (2013.01); *A61B 5/02125* (2013.01);
(Continued)

(58) Field of Classification Search
CPC . A61B 5/352; A61B 5/02007; A61B 5/02125; A61B 5/333; A61B 5/35;
(Continued)

(56) References Cited

U.S. PATENT DOCUMENTS 9,579,060 B1    2/2017  Lisy et al.
2006/0074331 A1*  4/2006  Kim .................... A61B 5/7264
                                                        600/515
(Continued)

FOREIGN PATENT DOCUMENTS

TW    201626938 A    8/2016
WO    2001/066011 A2  9/2001
(Continued)

OTHER PUBLICATIONS

United Kingdom Search Report dated Mar. 29, 2018, received for corresponding UK Application No. GB1717092.9, 5 pages.
(Continued)

*Primary Examiner* — Scott M. Getzow
(74) *Attorney, Agent, or Firm* — Kinney & Lange, P.A.

(57) ABSTRACT

The disclosure relates to a device and method of obtaining an electrocardiogram for a subject. The method comprises receiving electrical signals from at least two head-mounted sensors; and analysing said electrical signals to resolve shape and timing information for each of the P-, Q-, R-, S-, and T-waves available for the subject over a number of cardiac cycles, to derive a composite electrocardiogram, ECG, in which the composite electrocardiogram is derived using signals only from said head-mounted sensors.

22 Claims, 11 Drawing Sheets

(51) Int. Cl.
  *A61B 5/35*   (2021.01)
  *A61B 5/333*  (2021.01)
  *A61B 5/02*   (2006.01)
  *A61B 5/021*  (2006.01)

(52) U.S. Cl.
  CPC ............... *A61B 5/333* (2021.01); *A61B 5/35* (2021.01); *A61B 5/6803* (2013.01); *A61B 5/6817* (2013.01); *A61B 2562/0204* (2013.01)

(58) Field of Classification Search
  CPC ............... A61B 5/6803; A61B 5/6817; A61B 2562/0204; A61B 5/332; A61B 5/349; A61B 5/6814; A61B 5/6815; A61B 5/318
  See application file for complete search history.

(56) References Cited

U.S. PATENT DOCUMENTS

| | | | |
|---|---|---|---|
| 2006/0173373 A1* | 8/2006 | Shin | A61B 7/04 600/513 |
| 2008/0171945 A1 | 7/2008 | Dotter | |
| 2013/0144130 A1* | 6/2013 | Russell | A61B 5/335 600/301 |
| 2014/0051939 A1 | 2/2014 | Messerschmidt | |
| 2016/0089047 A1* | 3/2016 | Jonnada | A61B 5/333 600/521 |
| 2016/0089086 A1* | 3/2016 | Lin | A61B 5/02416 600/479 |
| 2016/0259986 A1 | 9/2016 | Yun et al. | |
| 2017/0035323 A1 | 2/2017 | Elberse et al. | |
| 2017/0042434 A1 | 2/2017 | Dias Júnior et al. | |
| 2017/0258336 A1* | 9/2017 | Furness, III | A61B 5/026 |
| 2020/0196977 A1* | 6/2020 | Martin | A61B 7/003 |

FOREIGN PATENT DOCUMENTS

| | | |
|---|---|---|
| WO | 0166011 A2 | 9/2001 |
| WO | 2009005734 A2 | 1/2009 |
| WO | 2012068613 A1 | 5/2012 |
| WO | 2012108895 A1 | 8/2012 |
| WO | 2015107339 A1 | 7/2015 |
| WO | 2016145438 A1 | 9/2016 |

OTHER PUBLICATIONS

International Search Report and Written Opinion dated Apr. 21, 2020, received for corresponding PCT Application No. PCT/GB2018053021, 16 pages.
Tsu-Wang Shen, Tim Hsiao, Yu-Tsung Liu, and Tsung-Ying He, An Ear-Lead ECG Based Smart Sensor System with Voice Biofeedback for Daily Activity Monitoring, Deparlment of Medical Informatics, Tzu Chi University, Taiwan, 2008, 8 pages.
Wesley Banks, P.E., The Complete Guide to Hearable Technology, Everyday Hearing Blog, 7 pages.
Wilhelm Von Rosenberg, Theerasak Chanwimalueang, Valentin Goverdovsky, David Looney, David Sharp, and Danilo O. MANDIC, Smart Helmet: Wearable Multichannel ECG and EEG, IEEE Journal of Translational Engineering in Health and Medicine, 2016, 11 pages.
Valentin Goverdovsky, Wilhelm Von Rosenberg, Takashi Nakamura, David Looney, David J. Sharp, Christos Papavassiliou, Mary J. Morrell, & Danilo O. Mandic, Hearables: Multimodal Physiological in-ear sensing, Scientific Reports, 2017, 10 pages.
Wilhelm Von Rosenberg, Theerasak Chanwimalueang, Valentin Goverdovsky, Nicholas S. Peters, Christos Papavassiliou & Danilo O. Mandic, Hearables: feasibility of recording cardiac rhythms from head and in-ear locations, Royal Society Open Science, 2017, 13 pages.
Mikey Campbell, Apple patents sensor-packed health monitoring headphones with 'head gesture' control, 2014, 8 pages.
David Da He, Eric S. Winokur, & Charles G. Sodini, An Ear-Worn Vital Signs Monitor, IEEE Transactions on Biomedical Engineering, vol. 62, No. 11, Nov. 2015, 6 pages.
Great Britain Examination Report dated Dec. 10, 2021, received for corresponding Great Britain Application No. 1717092.9, pp. 6.
Examination Report dated Jun. 9, 2022, received for corresponding European Application No. 18795763.4 (8 pages).
International Search Report and Written Opinion dated Dec. 12, 2018, for corresponding PCT Application No. PCT/GB2018/053021.

* cited by examiner

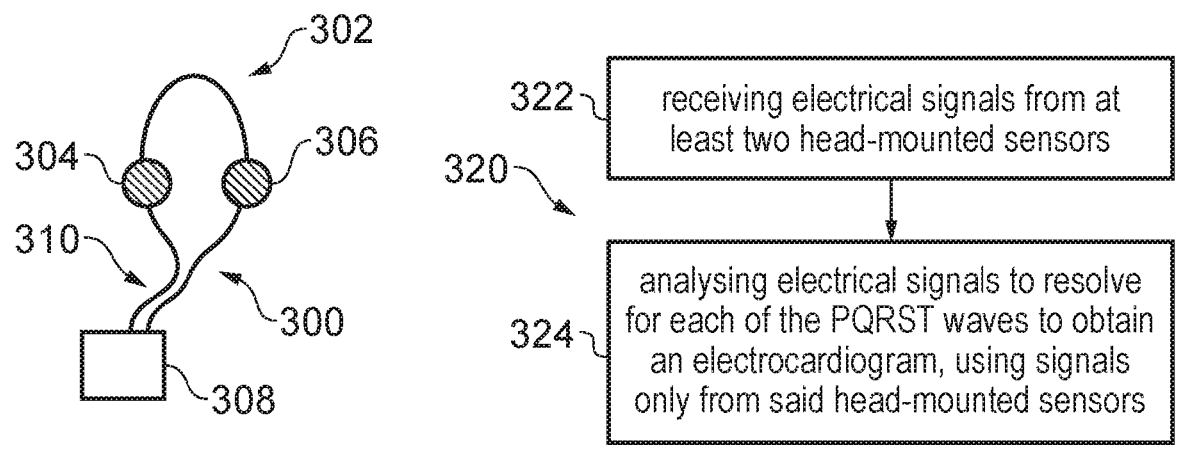
FIG. 3a
FIG. 3b
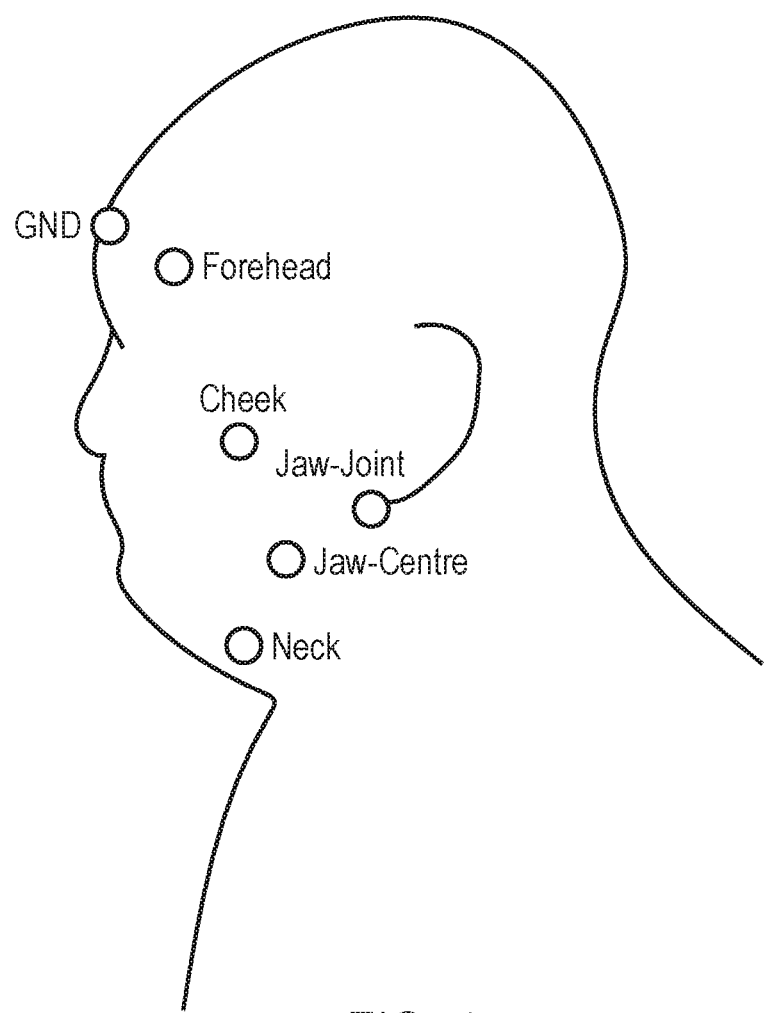
FIG. 4

ELECTROCARDIOGRAM APPARATUS AND METHOD

CROSS-REFERENCE TO RELATED APPLICATION(S)

The present application is the national phase of PCT Application No. PCT/GB2018/053021 filed on Oct. 18, 2018, which in turn claims priority to British Application No. 1717092.9 filed on Oct. 18, 2017, both of which are incorporated by reference herein in their entireties.

BACKGROUND

The disclosure relates to an apparatus and associated method for obtaining an electrocardiogram of a subject. In particular, although not exclusively, the disclosure relates to obtaining ECG data from head-mounted sensors.

In recent years there has been a rapid development of wearable devices for measuring vital signs and neural signals, for both medical and recreational purposes. For user convenience, devices that are inconspicuous and discreet, or those which make use of the appliances or clothing already worn by the user, are most suitable. State-of-the-art wearable devices for recording cardiac signals include: (i) wrist bands, whereby the heart rate is typically recorded through a photoplethysmogram (PPG), or (ii) chest straps which record a standard electrocardiogram (ECG). However, PPG is suitable only for measuring the heart rate and recording an ECG from the wrists requires cables running between the arms, while chest straps can be obtrusive and stigmatising. This makes these current solutions unsuitable for many real-world applications.

SUMMARY

According to a first aspect of the disclosure there is provided a method of obtaining an electrocardiogram for a subject, the method comprising:
 i. receiving electrical signals from at least two sensors, the at least two sensors including at least two electrodes, in which all of the at least two electrodes are head-mounted electrodes; and
 ii. analyzing said electrical signals over a plurality of cardiac cycles to derive a composite electrocardiogram with shape and timing information for each of the P-, Q-, R-, S- and T-waves available for the subject.

The composite electrocardiogram may be obtained using signals only from said at least two sensors. The at least two sensors may be head-mounted sensors. The composite electrocardiogram may be obtained by the processing module using signals only from head-mounted sensors.

A composite electrocardiogram may also be referred to as a compound electrocardiogram or combined electrocardiogram. The plurality of cardiac cycles may be a plurality of different cardiac cycles. Each of the plurality of cardiac cycles may occur at a different time from the other cardiac cycles. The plurality of cardiac cycles may comprise a sequence of cardiac cycles.

The electrical signals may be analog electrical signals. The electrical signals may be digital electrical signals or sampled data.

The received electrical signals from the at least two sensors may derive from a left in-ear electrode and from a right in-ear electrode. The received electrical signals may further include electrical signals from at least a third head-mounted electrode. The third head-mounted electrode may comprise an electrode disposed on the head in one of the positions: jaw, mastoid, concha, and forehead. The received electrical signals may further include electrical signals from the third electrode disposed within one of the left ear or the right ear canal.

The at least two electrodes may comprise electrodes that are disposed on opposite sides of the sagittal plane to serve as a proxy for a body-mounted Lead I ECG electrode array. The at least two electrodes may comprise electrodes that are disposed symmetrically on opposite sides of the sagittal plane.

Analyzing said electrical signals may comprise determining locations, or timestamps (occurrence times), of R-waves in the electrical signals corresponding to plural cardiac cycles. Analyzing said electrical signals may comprise, based on the R-wave locations, aligning multiple sets of data samples, each set of data samples corresponding to a different cardiac cycle. Analyzing said electrical signals may comprise combining the multiple data samples over the plural cardiac cycles to resolve any P-, Q-, S- and T-waves in the received electrical signals. The locations of R-waves in the electrical signals may be determined by matching successive data samples against a predetermined template. The locations of R-waves in the electrical signals may be at least partially determined by finding the positions of maxima in the electrical signals. The location of a subsequent R-wave may be determined based on the determined position of a previous R-wave. The locations of R-waves may be determined based on a combination of the above approaches.

The at least two sensors may include at least two electrodes and at least one additional sensor. A potential time window for the R-waves for each of the number of cardiac cycles may be determined using a signal from the at least one additional sensor. The at least one additional sensor may comprise at least one non-electrode sensor, non-electrical sensor or non-ECG sensor.

The at least one additional sensor may comprise a mechanical, acoustic, or optical sensor. The at least one additional sensor may comprise at least one microphone or other mechanical transducer. A signal from the non-electrode sensor may be used to denoise the measured composite electrocardiogram.

A time difference between features in the electrocardiogram and the additional sensor may be used to calculate the pulse wave velocity. The additional sensor may be used to obtain a pulse waveform. The pulse wave velocity or pulse waveform may be used to calculate arterial stiffness or other cardiovascular parameters. Cardiovascular parameters may be calculated using the waveform of at least one signal modality (e.g. acoustic, mechanical or optical) and/or the time differences between features in at least two modalities by applying deterministic, for example, or machine-learning techniques.

In the simultaneous recordings of ECG and the at least one additional sensor, the combination of the signals from all modalities may be used to calculate the pulse wave velocity and the pulse waveform. Both are indicators for arterial stiffness, which itself is an indicator for cardiovascular diseases.

The method may comprise automatically comparing the composite electrocardiogram with one or more template patterns associated with a known cardiovascular state in order to determine whether the composite electrocardiogram corresponds to a known cardiovascular state. The one or more known cardiovascular states may comprise one or more known cardiovascular diseases or irregularities. The one or more known cardiovascular states may comprise a healthy state. The method may comprise transmitting a message to a user in the event that a disease or irregularity is identified.

The method may comprise applying an adaptive or other algorithm to register the subject's normal cardiac cycle. The method may comprise comparing the normal cardiac cycle with an ECG for one or more subsequent cycles (or future cardiac cycles) in order to identify any deviations from the normal cardiac cycle.

The method may comprise storing the observed cardiac cycles and/or the derived ECG.

The at least two electrodes may comprise electrodes that are disposed symmetrically on opposite sides of the coronal plane to serve as a proxy for front-to-back electrocardiogram.

The method may comprise receiving electrical signals from a plurality of pairs of electrodes, each pair of electrodes defining a channel signal. Each electrode may be part of multiple pairs of electrodes. The method may comprise generating a virtual channel from the plurality of channel signals. The method may comprise deriving the composite electrocardiogram from a plurality of cardiac cycles in the virtual channel. The method may comprise generating a combined channel from the plurality of channel signals. The method may comprise deriving the composite electrocardiogram from a plurality of cardiac cycles in the combined channel.

According to a further aspect there is provided a processing module for obtaining an electrocardiogram, ECG, of a subject, configured to:
  i. receive electrical signals from at least two sensors, the at least two sensors including at least two electrodes, in which all of the at least two electrodes are head-mounted electrodes;
  ii. analyze said electrical signals to resolve shape and timing information for each of the P-, Q-, R-, S- and T-waves available for the subject over a number of cardiac cycles, to derive a composite electrocardiogram.

The composite electrocardiogram may be obtained by the processing module using signals only from said at least two sensors. The composite electrocardiogram may be obtained by the processing module using signals only from head-mounted sensors.

According to a further aspect, there is provided a device for obtaining an electrocardiogram for a subject, comprising the processing module and at least two electrodes for mounting on the subject's head.

The device may comprise a headset within which the at least two sensors are mounted. The at least two sensors may include at least two electrodes and at least one additional sensor. The processing module may be further configured to determine a potential time window for the R-waves for each of the number of cardiac cycles using a signal from the at least one additional sensor. The processing module may be further configured to attempt to detect an R-wave within each of the potential timing windows.

According to a further aspect there is provided a computer program configured to cause a processor to perform the method. The computer program may be stored on a non-transient storage medium.

According to a further aspect there is provided a method of obtaining an electrocardiogram for a subject, the method comprising:

i. receiving electrical signals from at least two sensors, the at least two sensors including at least two electrodes, in which all of the at least two electrodes are head-mounted electrodes; and
ii. analyzing said electrical signals over at least one cardiac cycle to derive an electrocardiogram with shape and timing information for each of the P-, Q-, R-, S- and T-waves available for the subject.

According to a further aspect there is provided a method of obtaining an electrocardiogram for a subject, the method comprising:
  i. receiving electrical signals from at least three sensors, the at least three sensors including at least three electrodes, in which all of the at least three electrodes are positioned on the head of the subject and define a plurality of pairs of electrodes, each pair of electrodes defining a channel signal; and
  ii. analyzing said electrical signals over a plurality of cardiac cycles to derive an electrocardiogram with shape and timing information for each of the P-, Q-, R-, S- and T-waves available for the subject. All of the at least three electrodes may be positioned in the ear or ears of the subject. In general, the method may be used in combination with any feature described herein.

According to a further aspect there is provided a device for obtaining an electrocardiogram for a subject, comprising:
  i. at least three electrodes for mounting on the subject's head and defining a plurality of pairs of electrodes, each pair of electrodes defining a channel signal;
  ii. a processing module for obtaining an electrocardiogram, ECG, of the subject, configured to:
  iii. receive electrical signals from at least three sensors, the at least three sensors including the at least three electrodes; and
  iv. analyzing said electrical signals over a plurality of cardiac cycles to derive an electrocardiogram with shape and timing information for each of the P-, Q-, R-, S- and T-waves available for the subject. The at least three electrodes are configured to be mounted in one or both of the subject's ears. In general, the method may be used in combination with any feature described herein.

BRIEF DESCRIPTION OF THE DRAWINGS

Embodiments of the present disclosure will now be described by way of example and with reference to the accompanying drawings in which:

d. FIG. 3a illustrates a schematic of a device for obtaining an electrocardiogram from the head of a subject;

e. FIG. 3b illustrates a method for obtaining an electrocardiogram for a subject;

f. FIG. 4 illustrates example positions for mounting electrodes on the head of a subject;

DETAILED DESCRIPTION

The present disclosure relates to a method and apparatus for obtaining an electrocardiogram of a subject (e.g. a patient or user) using wearable electrodes placed on the subject's head. The head is in a relatively stable position with respect to the vital signs in most daily activities, such as sitting, walking or sleeping. A smart helmet with embedded sensors may be used to record cardiac and neural signals in real-world scenarios from various locations on the head, while avoiding the use of electrodes mounted on the body.

Figure 1:
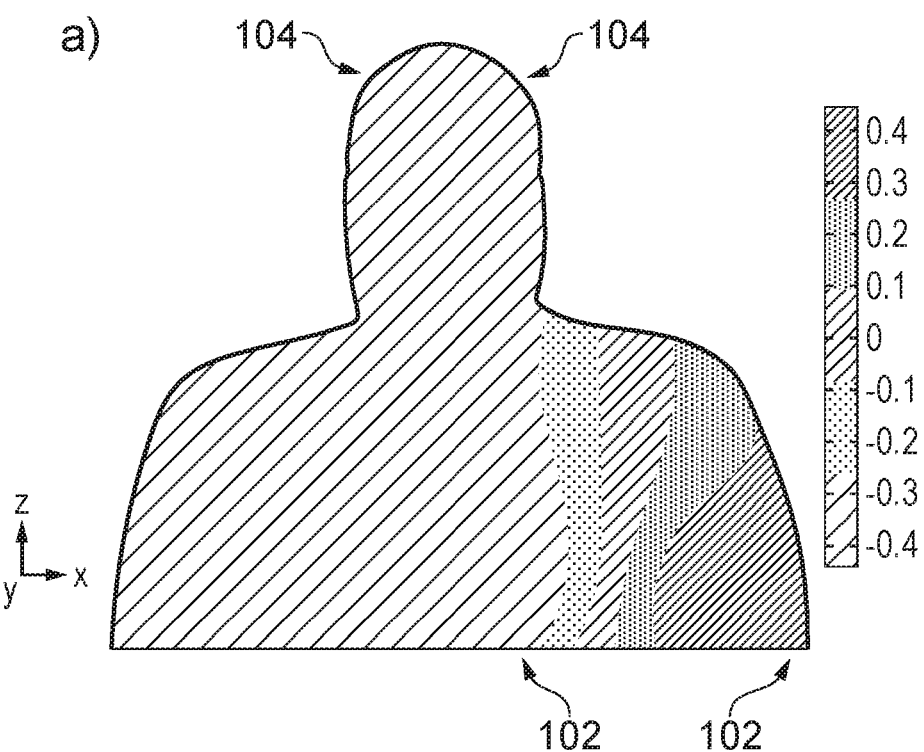
FIG. 1 shows a snapshot of simulated cardiac potentials on the upper torso and the head.

FIG. 1 shows a profile of simulated cardiac potentials on the upper torso and the head of a subject at 'time zero' of the cardiac cycle, that is, the time of the peak of an R-wave. The figures shown on the scale bar are in units of millivolts. There is a significant potential difference 102 across the torso and arms (first (red) vs. second (blue) surface) but a very much smaller potential difference 104 across the head. This difference between electrical distribution across the body and across the head poses a difficulty for using head-mounted electrodes to obtain ECG readings; the signal-to-noise ratio of head-based measurements is typically 1-2 orders of magnitude inferior to that obtained from measurements taken from the torso. For head-ECG recordings, signal quality may be strongly dependent on: (i) the positioning of the electrodes and (ii) the skin-electrode contact impedance. With appropriate electrodes and electrode positioning, the detection of an R-wave (see FIG. 2b below), the most prominent feature in a cardiac cycle, using head-mounted electrodes (or elsewhere) can be possible. The signal-to-noise ratio is such that it is feasible to reliably extract the timing of QRS-complexes using head-mounted electrodes. However, it has been found to be not possible to determine a full electrocardiogram (including identifiable P- to T-waves) for a particular cardiac cycle using only head-mounted electrodes due to the inferior signal-to-noise ratio measured at the head.

It is useful to obtain ECG information such as timings of R-waves in the signal because this enables heart rate monitoring. Indeed, many cardiac measurement devices that claim to be ECG monitors are in fact merely a heart rate monitor utilizing R-wave detection. The inability to reliably obtain full ECG waveforms (including the timing and shape of the P-, Q-, S-, and T-waves) using head-based measurements has hitherto limited the practical applications for such monitoring devices.

One way to improve the signal-to-noise ratio of a measurement using a head electrode is to combine it with a measurement taken using a body electrode (for example, a measurement taken from the left ear to the right arm). However, such implementations do not benefit from the full advantages regarding the user convenience of using only head electrodes because, by necessity, an electrode and connecting cable is required on the subject's body.

Figure 2:
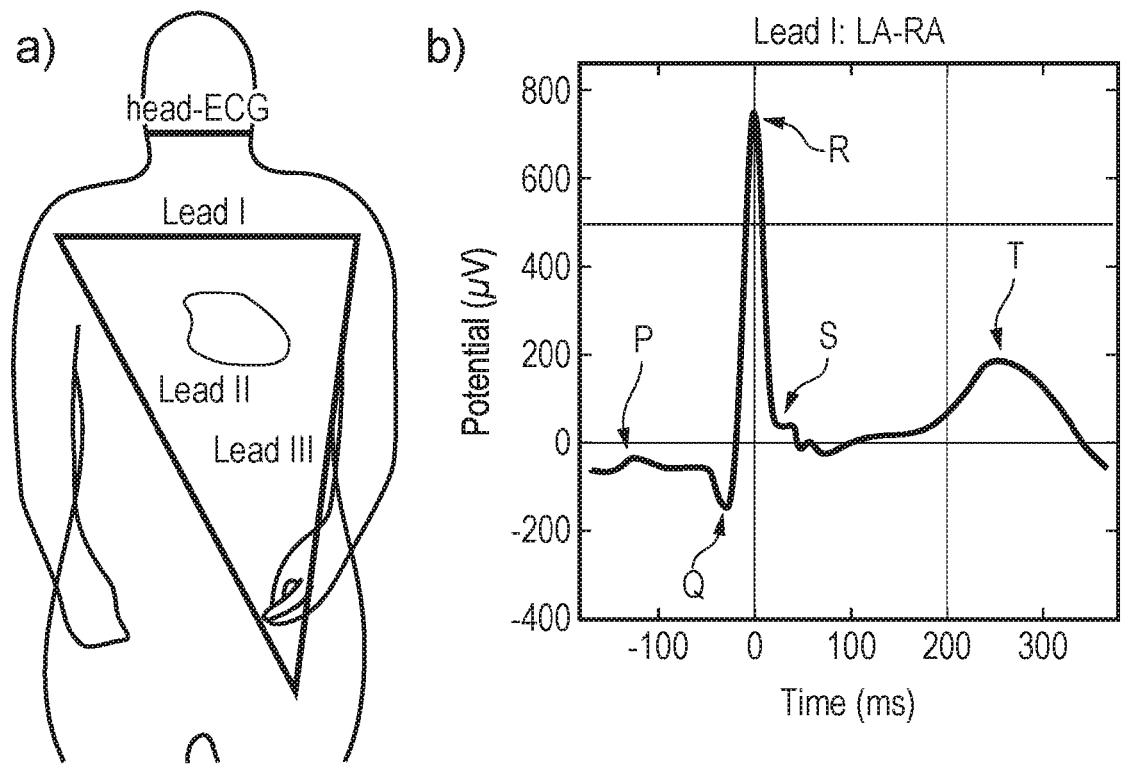
FIG. 2a illustrates a schematic diagram of the standard Lead I, Lead II and Lead III electrode configurations on the torso of a subject and a generic head-ECG channel.
FIG. 2b illustrates a typical electrocardiogram taken using a Lead I configuration.

FIG. 2a illustrates a schematic diagram of various standard electrode configurations on a torso of a subject. Electrodes are placed at the ends of the lines denoting the various configurations. The configurations include: (i) a Lead I configuration in which electrodes are disposed to measure a potential difference across the torso (horizontally for a standing subject); (ii) a Lead II configuration in which electrodes are disposed to measure a potential difference diagonally across the torso; and (iii) a Lead III configuration in which electrodes are disposed to measure a potential difference along the torso (vertically for a standing subject).

FIG. 2b illustrates a typical electrocardiogram taken using a Lead I configuration between the left and right arms of across the torso of a subject. The positions of P-, Q-, R-, S- and T-waves are labelled. The Lead I configuration is of interest for many clinical purposes, including the diagnosis of a range of cardiovascular diseases, and is comparatively well recognised by clinicians. It is therefore preferable to employ electrode configurations that provide a proxy for a Lead I ECG signal. Determining a potential using an electrode on the head and another electrode on the body does not typically result in a proxy for a Lead I arrangement.

FIG. 3a illustrates a schematic block diagram of a device 300 for obtaining an electrocardiogram for a subject. The device 300 comprises at least two sensors 304, 306 for mounting on the subject's head, and a processing module 308. The at least two sensors 304, 306 in this example are each provided by an electrode and are electrically coupled to the processing module 308 via respective cables 310. Electrodes such as those described in US 2016/0331328 may be used. The device may comprise a headset 302 on which the at least two sensors 304, 306 are mounted. The cables 310 may also be part of the headset 302. The headset 302 may comprise, for example, a helmet, a hat, a pair of headphones, a pair of earphones, a pair of hearing aids, or a headband. The at least two sensors 304, 306 may be provided by respective in-ear electrodes on headphones, for example. One sensor 304 may provide a right ear electrode and another sensor 306 may provide a left ear electrode.

For example, hearing-aid type hard earplugs or smart devices such as those described in US 2012/0177233 may be used. Hearing aids typically have an on-board microcomputer. Where left and right ear hearing aids are connected by a cable, all the calculation can be performed on one or both of the hearing aids. The output of calculation may be used to alert the user using a speaker on hearing aid or may be transmitted elsewhere (e.g. wirelessly to a smart phone or computer using conventional means).

The device 300 may further comprise a third or more head-mounted electrodes. The device 300 may also comprise other types of sensors (non-electrode sensors—not shown) for mounting on the subject, which may be built into the headset 302. The other types of sensors that may be used with a plurality of electrodes include microphones or other mechanical sensors, ballistocardiogram sensors, mechanical plethysmogram sensors and photoplethysmogram sensors, for example. The speaker of a headphone may also be used as a microphone. In the case that one or more additional (non-electrode) sensors are comprised in a unit that is configured to be positioned on the body of the subject (other than on the head), the unit may be further configured to communicate wirelessly with the processing module 308. For example, an additional sensor may be mounted in a wrist watch and wirelessly communicate with a device comprising head mounted sensors, whilst still achieving the advantages of solely using head-mounted electrodes.

FIG. 4 illustrates a schematic profile of the head of a subject labelled with potential sites for placement of a head electrode. Labelled sites for the head electrodes include the forehead, cheek, jaw-joint, jaw-centre and neck, which is considered to be part of the head for the purpose of electrode placement. Other sites may also be possible.

The electrodes for the head may be attached symmetrically across the sagittal plane, and locations for the electrodes include both sides of the neck (for example, under the strap of a motorcycle helmet), the centre of the left and right parts of the lower-jaw, the jaw-joints, the jaw-centre, the cheeks, and both sides of the forehead. A ground electrode (GND) may be placed in the middle of the forehead, an ear canal or elsewhere on the head. Electrodes in such locations may be attached to the lining of a helmet at positions where the lining firmly touches the head. Head-ECG channels may be monitored using standard passive gold cup electrodes (10 mm diameter) and conductive gel or alternatively any active electrode or a flexible electrode comprising a conductive fabric, or any other electrode.

In some examples, "front-to-back" signals, i.e. signals taken from positions on either side of the coronal plane, may be obtained from head-mounted electrodes in order to provide a proxy of the conventional front-to-back component of the heart vector (electrocardiogram).

Returning to FIG. 3b, a method 320 of obtaining an electrocardiogram for a subject is illustrated. The method 320 may be implemented by the processing module 308 of the device described previously with reference to FIG. 3a, for example. The method 320 comprises receiving electrical signals from at least two sensors (box 322) and analyzing said electrical signals (box 324) to resolve shape and timing information for each of the P-, Q-, S- and T-waves available for the subject over a number of cardiac cycles, to derive a composite electrocardiogram. The composite electrocardiogram is obtained using signals only from the sensors, which include at least two head-mounted electrodes. Obtaining the composite electrocardiogram does not involve analyzing any signals from electrodes mounted on the subject other than on the head. For example, two head-mounted electrodes may be disposed symmetrically on opposite sides of the sagittal plane to serve as a proxy for a body-mounted Lead I ECG electrode array.

Analyzing the electrical signals may comprise:
i. determining locations of R-waves in the electrical signals for plural cardiac cycles of the subject;
ii. based on the R-wave locations, aligning multiple windows of data samples each corresponding to a cardiac cycle; and
iii. combining the multiple data samples over the plural cardiac cycles to resolve any P-, Q-, S- and T-waves in the electrical signals, in addition to the R-wave. In this way, data from a plurality of cycles are combined, a weighted averaging being the simplest way, resulting in an improvement in the signal-to-noise ratio that enables the P-, Q-, S- and T-waves to be resolved in cases where they are not distinguishable from a single cardiac cycle. The plural cardiac cycles of the subject include cycles that occur at different points in time. Such analysis may be conducted using successive heart cycles that are similar to one another. Inter-cycle waveform variations, both noise and variations in actual cardiac function, are removed. In this way, detailed electrocardiogram information is provided that was not hitherto available from head-ECG readings, enabling medical diagnostic information to be obtained using only head-mounted electrodes (optionally in combination with information from other types of sensor), thus avoiding the difficulties encountered with body-mounted electrodes.

The locations of R-waves in the electrical signals may be determined by matching successive samples against a predetermined template or by applying thresholding or peak detection techniques. A detailed example in which the locations of R-waves are determined is discussed below with reference to FIG. 8, and the combining of signals is discussed with reference to FIG. 9.

Figure 5:
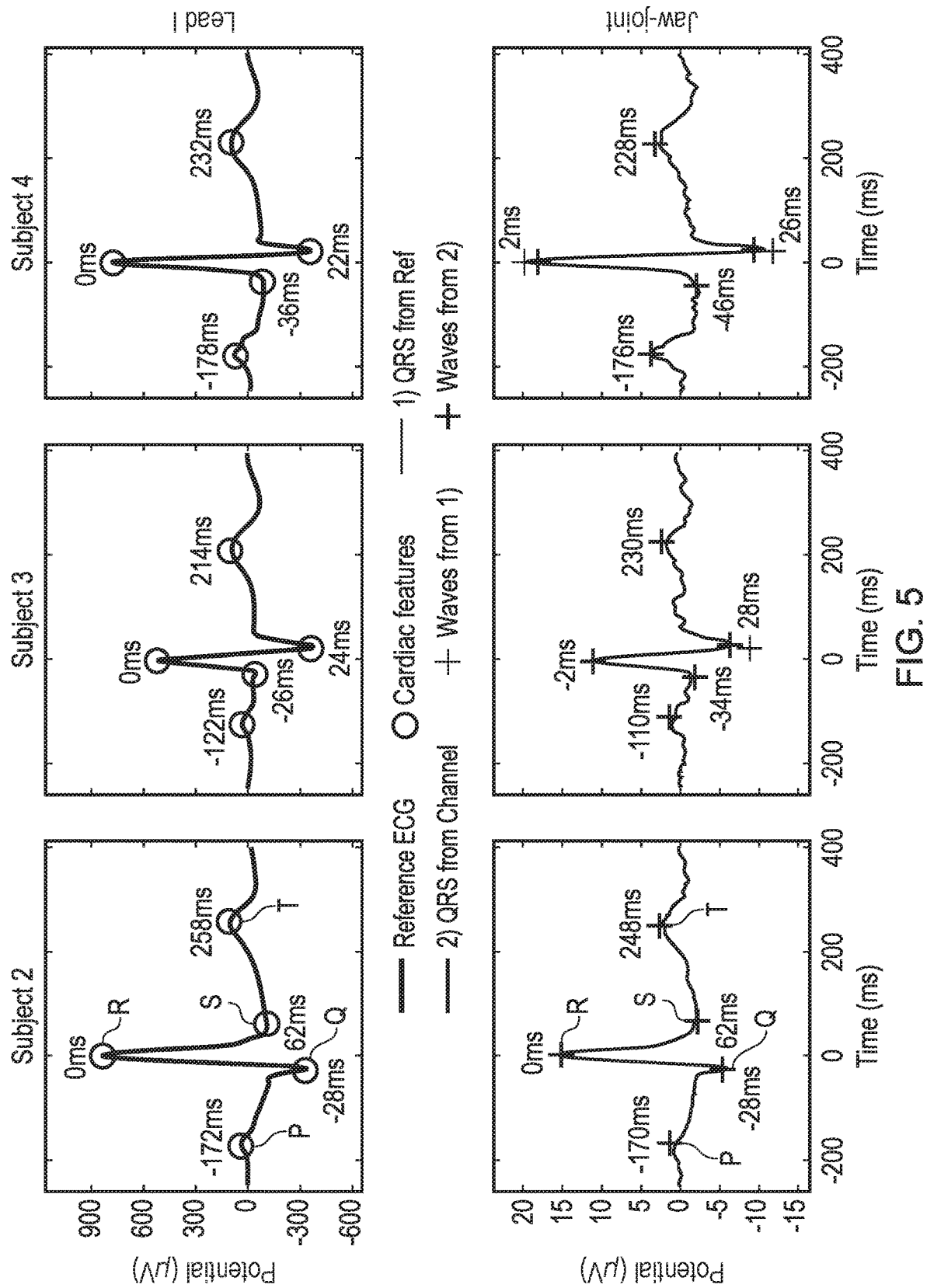
FIG. 5 illustrates a comparison between conventional Lead I ECG readings and corresponding jaw-joint ECG readings.
Figure 5:
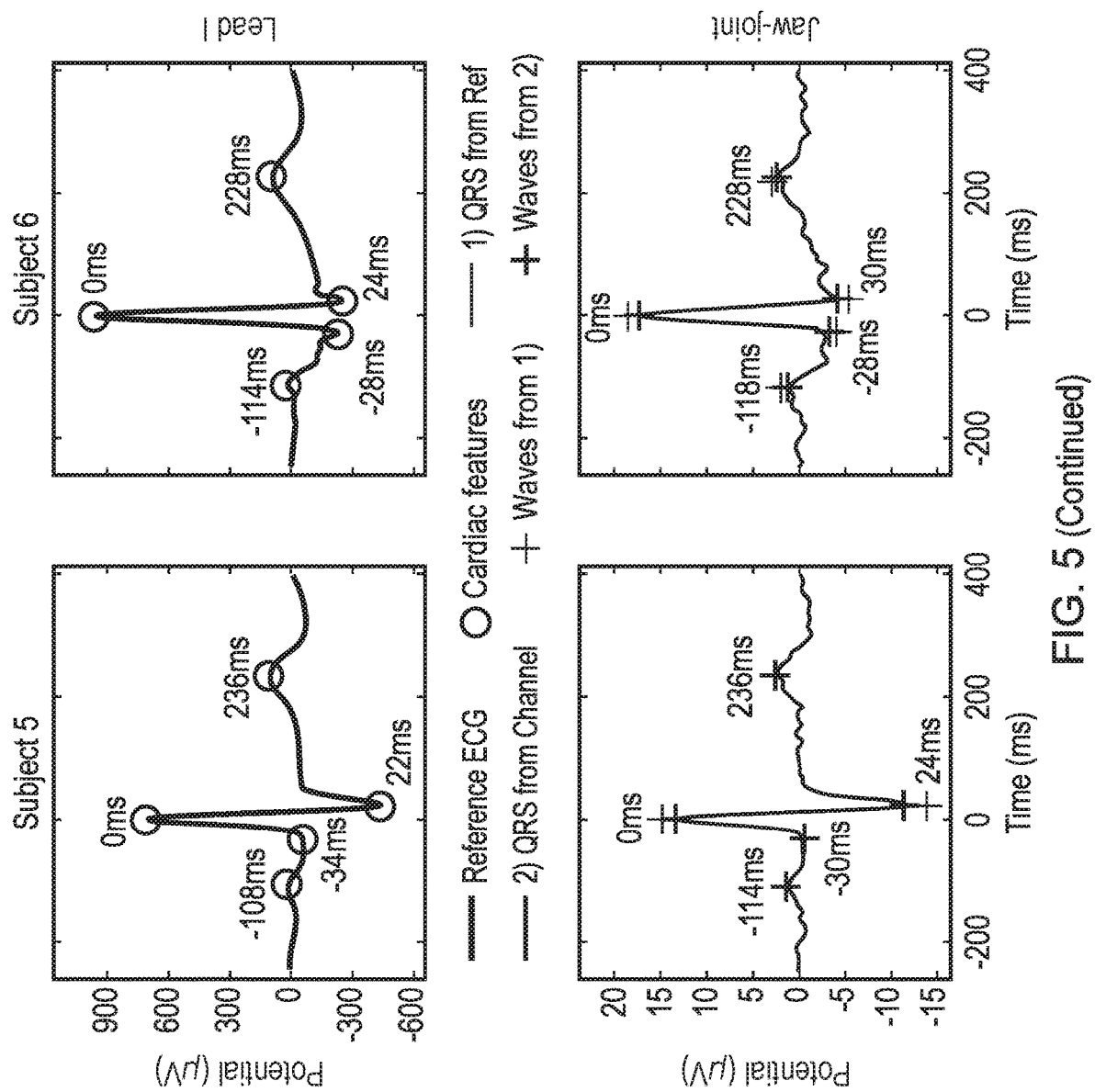
Figure 6:
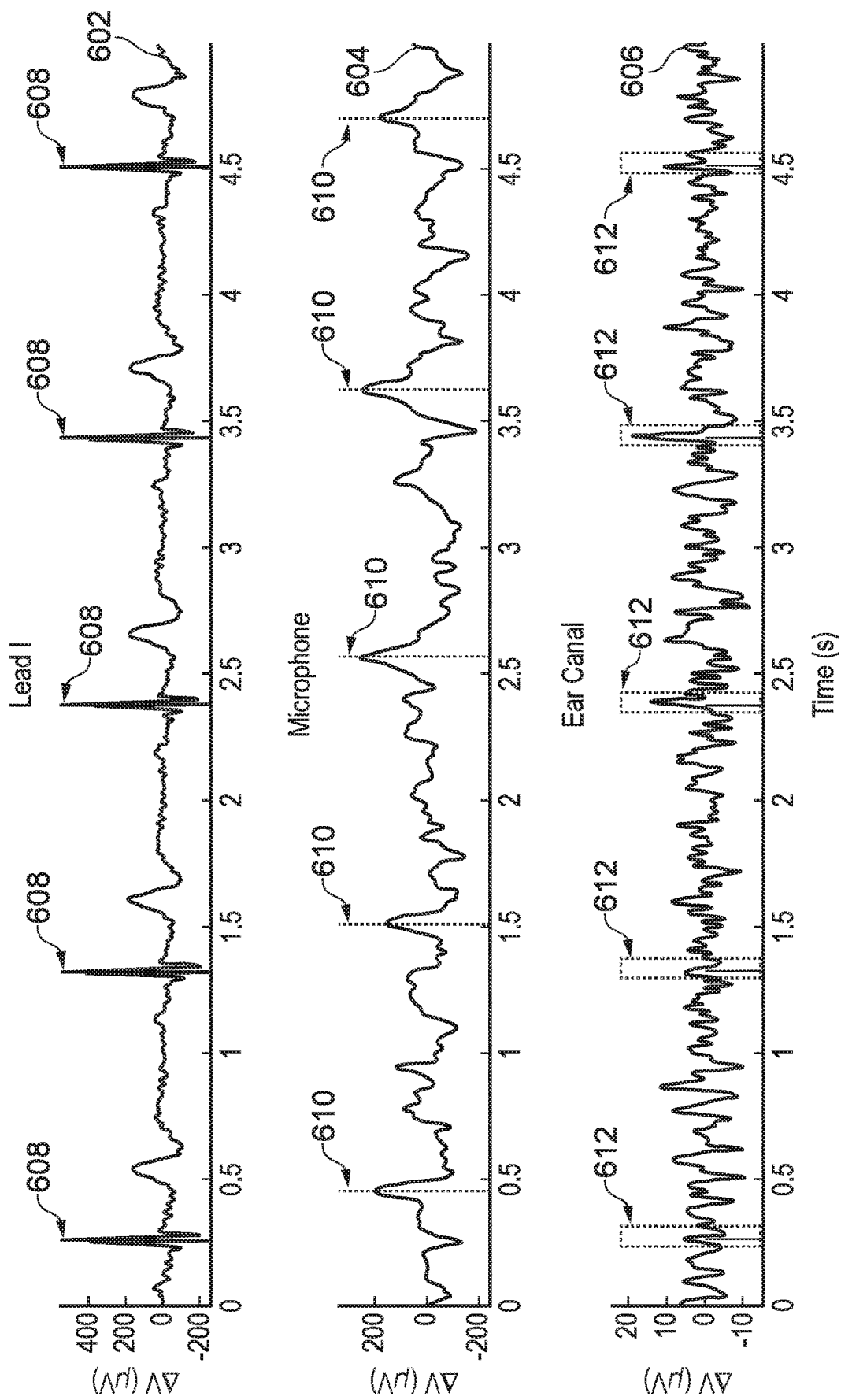
FIG. 6 illustrates signal profiles from a conventional Lead I ECG, an in-ear microphone, and an ear canal ECG.
Figure 7:
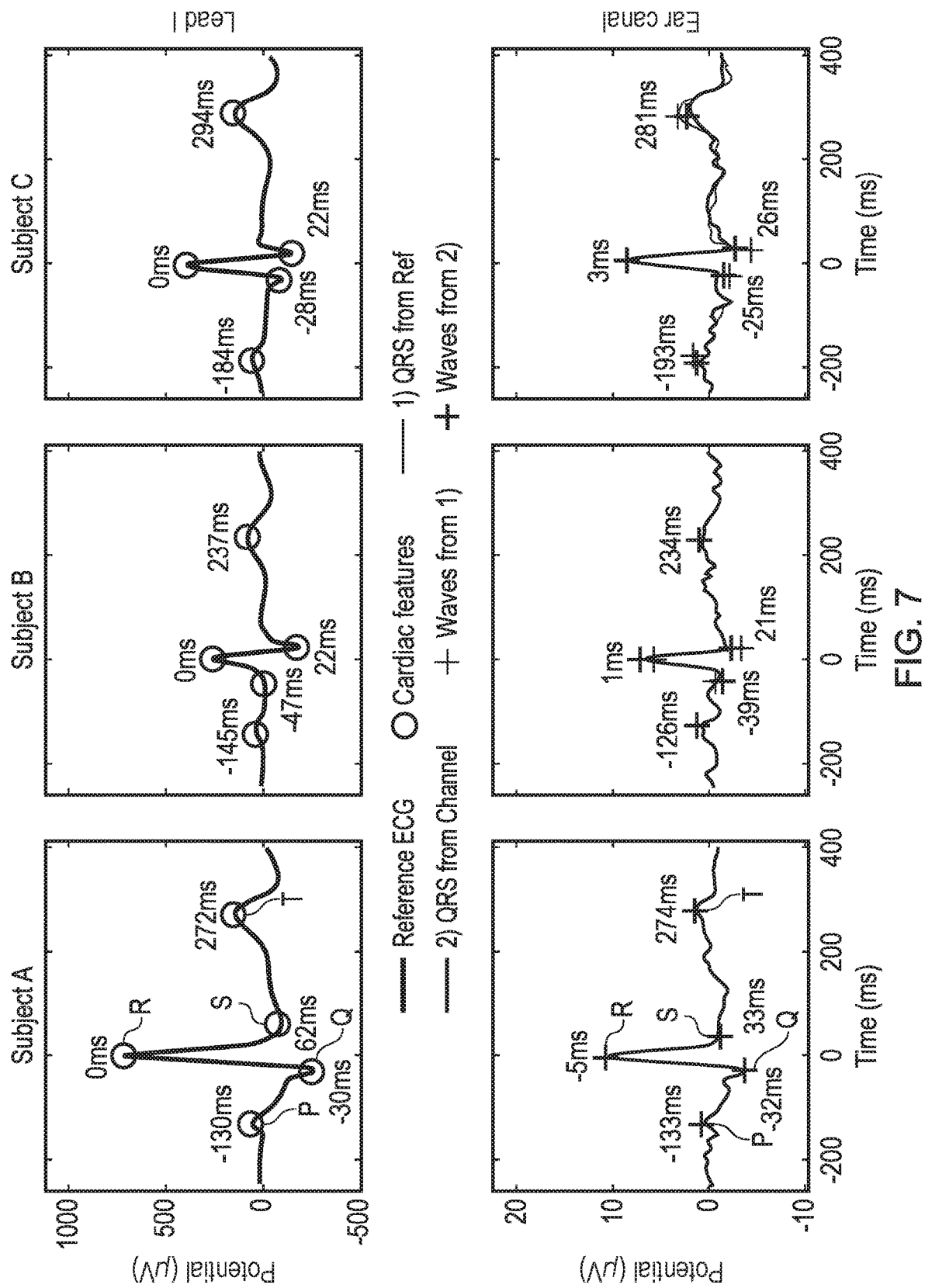
FIG. 7 illustrates a comparison between corresponding cardiac cycles from conventional Lead I ECG readings and ear canal ECG readings.
Figure 7:
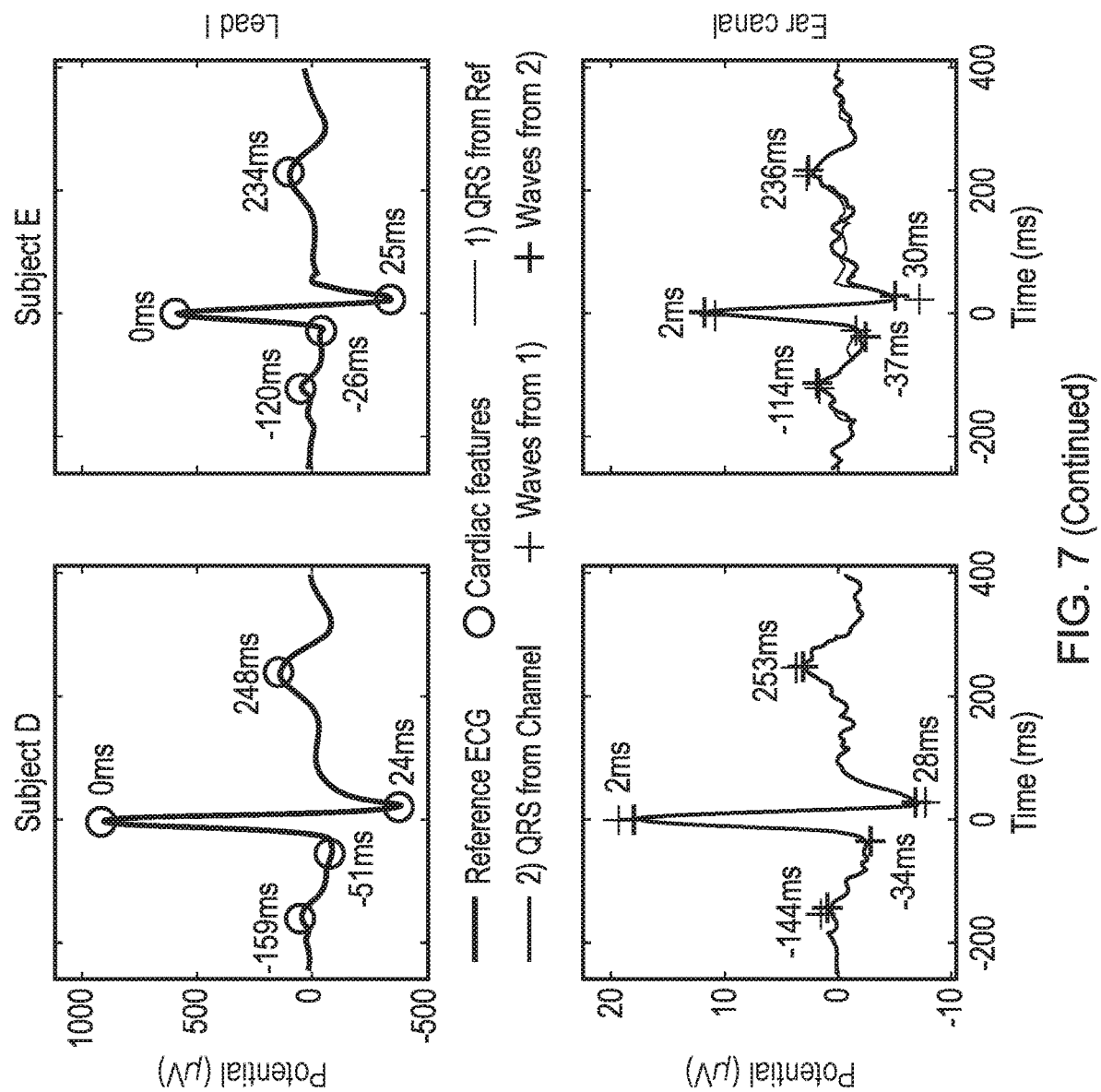

FIGS. 5 to 7 below describe the testing of a device configured to use the method of FIG. 3b and provide comparisons of ECG data obtained with conventional (torso) Lead I measurements taken for the same subjects.

In summary, the above described set-up according to FIG. 4 was tested for six subjects whose ECG was monitored for 180 s, so that the recorded time series contained between 167 and 245 heart beats (excluding the very first and last cardiac cycles in order to consider full cycles only). The processing steps for the recorded ECG signals are explained in Algorithm 1 (below), and consisted of the following procedures. R-wave extraction was applied to each head channel separately utilising a $3^{rd}$-order bandpass filter with a lower cut-off frequency of $f_{min}$=9 Hz and an upper cut-off frequency of $f_{max}$=28 Hz, applied to raw ECG before the R-waves were extracted. The timings of the identified R-waves in all channels and the original ECG-traces were used as inputs to a new function, which bandpass-filtered all traces using a $3^{rd}$-order bandpass filter with a lower cut-off frequency of $f_{min}$=3 Hz and an upper cut-off frequency of $f_{max}$=40 Hz. Subsequently, the sampling points in time windows around the QRS-complexes, starting 250 ms before and ending 400 ms after the "peaks" of the R-waves, were extracted in two different ways, using the R-wave timings as identified in:
1) the reference ECG from the arms (Lead I); and
2) the actual head-ECG channel under consideration.

Algorithm 1 Signal processing steps:
1) Record electric potential differences, raw_ECG, from six subjects for 3 min each, with one reference channel (arm-ECG, Lead I) and five ECG signal channels from the head.
2) Perform R-wave detection on all channels individually.
3) Bandpass-filter the signals in all channels in raw_ECG using a $3^{rd}$-order Butterworth filter with a lower cut-off frequency of $f_{min}$=3 Hz and an upper cut-off frequency of $f_{max}$=40 Hz, to give filtered_ECG.
4) Extract cardiac cycles around the identified R-waves (within a −250 ms to 400 ms window, where the R-wave may be attributed to a 0 ms positon) in each channel in two ways: 1) using the R-wave timings from the reference ECG from the arms (Lead I), and 2) using the R-wave timings obtained from the individual head- and ear-ECG channels themselves.
5) Combine the cardiac cycles for the two scenarios in Step 4 using a suitable signal processing or machine learning algorithm.
6) Calculate a suitable metric for the quality assessment of the individual channels, which may include:
   (i) root-mean-square error (RMSE) between the timings of the P-, Q-, R-, S-, and T-waves in the reference channel (Lead I) and a given head channel;
   (ii) the Pearson correlation coefficient between the cardiac cycles obtained using the head leads and Lead I;
   (iii) root-mean-square (RMS) of the ratios between the amplitude of the waves in the cardiac cycle and the amplitude of the R-wave in the same recording and channel; and
   (iv) root-mean-square error (RMSE) between the composite cardiac cycle of a given channel and all individual cycles recorded in the given same channel (based on the timing of the R-wave in the reference ECG), where the root-mean-square (RMS) was normalised by dividing by the standard deviation of the composite cardiac cycle.

The results of the four metrics are summarised in Table 1 and show the mean across six subjects. The electrode locations Neck, Jaw-centre, and Jaw-joint consistently exhibit the most faithful cardiac features for all the four applied metrics.

A comparison of the cardiac cycles from the head-ECG and the reference Lead I ECG from the arms is provided below in Table 1 in terms of: i) time differences between the cardiac features (the waves P-, Q-, R-, S- and T-waves in the cardiac cycle), ii) correlation of the cardiac cycles, iii) ratio between the amplitude of the waves and the amplitude of the R-wave in a given cycle, and iv) normalised variance. "Ref" denotes results for cardiac cycles for which the R-wave timings were obtained from the reference ECG (Lead I, on the arms), and "Sig" those for which the R-waves were obtained from the individual head channels themselves. The values represent the means across all six subjects, the first row displays the ideal values (the reference ECG compared to itself), and the highlighted row denotes the best overall performance.

quency components of the QRS-complex and therefore reduces the amplitude of the sharp of the QRS-complexes.

In head-ECG channels where the combined cardiac cycles are generated using R-wave timings from the same channel, and the head-ECG corresponds to the Lead I ECG, then both the QRS-complexes must have been identified correctly and all the information about the different patterns in the cardiac cycle must also have been present in the given head-ECG channel under consideration. For head-ECG channels where the combined cardiac cycle corresponds to the Lead I cardiac cycle only when R-wave timings were obtained from the reference ECG, the information about the cardiac cycle was still present in the head-ECG channel, but the noise level was too high to identify QRS-complexes correctly when using only a given individual channel.

For the two best quality head-ECG channels, the quantitative analyses indicate a slightly better performance when the timings of R-waves were taken from the reference ECG obtained from the arms. In other words, the quality of the cardiac cycles obtained from head-ECG can be further improved through an increased accuracy of the R-wave detection, e.g. by improving (reducing) the skin-electrode impedances or by advanced noise-reducing solutions. To enhance the overall signal quality while avoiding the need

TABLE 1

Comparison of cardiac cycles from jaw-joint-ECG and conventional Lead I ECG

| Channel | i) Time Difference | | ii) Correlation | | iii) Ampl. ratio | | iv) Var. |
|---|---|---|---|---|---|---|---|
| | Ref [ms] | Sig [ms] | Ref | Sig | Ref | Sig | |
| Reference | 0 | 0 | 1 | 1 | 1 | 1 | 0.11 |
| Neck | 9 | 7 | 0.94 | 0.95 | 2.31 | 2.16 | 2.05 |
| Jaw-centre | 8 | 8 | 0.97 | 0.97 | 1.94 | 1.80 | 1.60 |
| Jaw-joint | 9 | 6 | 0.98 | 0.97 | 1.95 | 1.74 | 1.40 |
| Cheek | 12 | 30 | 0.93 | 0.89 | 2.77 | 1.33 | 6.06 |
| Forehead | 29 | 36 | 0.52 | 0.82 | 6.15 | 1.68 | 9.89 |

In this example, each set of electrodes was placed symmetrically across the sagittal plane. For example, the 'neck channel' measurement set-up included one electrode placed on the left of neck and another electrode placed on the right of the neck. While the cardiac cycles of healthy people exhibit certain common features, e.g. the P-, Q-, R-, S-, and T-waves, the shape of these characteristic waves differs between people. To establish the feasibility of recording a head-ECG cardiac cycle, the form of which is similar to the standard Lead I on the arms, we conducted experiments over multiple subjects with diverse cardiac cycles.

FIG. 5 illustrates, for five subjects (subjects 2-6), head-ECGs including the timings of the P-, Q-, S-, and T-waves with respect to R-wave, as recorded from the Jaw-joints position (lower graphs) benchmarked against the simultaneously recorded reference Lead I arm-ECGs (upper graphs). The amplitude (which may be the mean or R-wave amplitude) in the reference ECG (from the arms) was approximately 50 times larger than the amplitude in the head channels. The pattern of the QRS-complexes varies between subjects, and the head-ECG accurately resembles various patterns in the corresponding ECG recorded using Lead I.

The timings of R-waves were not always exactly at 0 ms. This is due to different filter settings for determining the positions (locations), or timestamps, of the R-waves and for obtaining the full cardiac cycle (see Algorithm 1). Furthermore, a low-pass filter applied to the recorded signal to remove high-frequency noise also attenuates the high-frefor a reference ECG, an alternative way to detect QRS-complexes is to consider multiple head channels simultaneously and apply a suitable signal processing or machine learning algorithm. In this way, the accuracy in the multi-channel detection of QRS-complexes from only head-ECG becomes on par with using the reference ECG.

In summary, FIG. 5 and Table 1 show that cardiac cycles of subjects with different waveform patterns in the standard Lead I can be equally accurately obtained using only head-ECG electrodes.

FIG. 6 illustrates signal profiles, against time, from a conventional Lead I ECG (signal 602), from an in-ear microphone (signal 604), and from ECG electrodes placed within the ear canal (signal 606). The microphone is used primarily as a mechanical sensor, but also provides acoustic signals. The R-waves 608 in a signal are readily identifiable from the signal from the Lead I ECG 602 in a conventional way and are used for comparison.

The inner ear location is more convenient for health monitoring than helmet-worn sensors, as it enables unobtrusive recording of vital signs and EEG-traces in a wider range of scenarios. To establish the feasibility of ECG recordings from within the ear canal (ear-ECG), we used an earpiece with embedded sensors, with electrodes made from conductive fabric and microphones, and recorded cardiac signals from five subjects for four minutes in duration. The data were processed according to Algorithm 1 while the measurements from the microphones embedded in the ear-pieces were used to support the identification of the timings of QRS-complexes, as they are capable of detecting the tiny pulsations of blood vessels in the ear canal. Microphones are one example of mechanical displacement sensors used in an acoustic modality, alternative sensors that can be used include optical photoplethysmogram sensors and ballistocardiogram sensors. This approach is based on the delay between the peak of the R-wave and the maximum in the mechanical measurement from the microphone. The R-waves 612 identified using the signal 606 from the ear canal and the R-waves 610 identified using the signal 604 from the microphone are marked in FIG. 6. The R-wave detection window for the signal 606 from the ear canal can be limited to the interval, which may be between 220 ms and 140 ms in a typical subject, before the occurrence of a peak in the microphone signal, as shown in FIG. 6. That is, a potential timing window for the R-waves for each of the number of cardiac cycles may be determined based on a signal from the microphone. In some examples, a time difference between an identified R-wave and a corresponding acoustic, mechanical or optical signal may be determined for a particular patient during a cardiac cycle and that delay may be used to determine a detection window for R-waves in subsequent cardiac cycles for that patient. The knowledge of both an ECG and pulse arrival time as measured by, for example, a microphone, can be useful for determining other parameters. For example, the time delay between peaks in the at least two modalities and/or their waveforms can be an indicator for blood pressure. As a further example, the pulse wave velocity or the pulse waveform can be calculated from simultaneous microphone and ear-ECG recordings. Both the pulse wave velocity and the pulse waveform are indicators for arterial stiffness, which itself is an indicator for cardiovascular diseases. Blood pressure, arterial stiffness and other cardiovascular parameters may be calculated from at least one of electrical, mechanical, acoustic and optical signals, their waveforms and/or time delays using deterministic or machine-learning techniques.

An electromechanical sensor, such as a microphone may be used in both ears to obtain two mechanical signals in addition to the signal from the electrodes. The two mechanical signals can then be used to give more precise information about the timing of the expected R-peak from the noisy ear-ECG. In general, a plurality of non-electrode sensors (of the same or different types) may be provided in both ears (for example, one or more microphones or PPG sensors (IR optocouplers) on each earplug) so that information from such sensors can be combined with one or more ear-ECG channels.

A plurality of in-ear electrodes may also be provided in each ear in order to form a plurality of pairs of electrodes across the head. Each pair of electrodes is associated with a different ECG channel. The plurality of channels can be combined to create a virtual channel (as discussed below with reference to FIG. 8) in order to reduce signal noise. The use of the virtual channel may reduce the number of cycles that need to be considered to create a combined cycle (averaged over different temporal cycles) of sufficient signal quality. In general, different head-ECG channels can be combined to estimate cardiac cycles: i) by combining ECG across the "spatial" channels for each cardiac cycle, ii) by combining across spatial channels over several consecutive cardiac cycles.

FIG. 7 presents the combined ear-ECG cycles, produced by using a suitable signal processing or machine learning algorithms, with weighted averaging being a simple linear case. FIG. 7 is similar to FIG. 5 in that it provides a comparison between conventional ECG readings and corresponding head ECG readings. In this case, the head ECG is taken using electrodes in the opposing ear canals. The electrodes were made from conductive fabric and embedded on ear pieces. FIG. 7 illustrates, for five subjects, ear-ECGs including the timings of the P-, Q-, S-, and T-waves with respect to R-wave, as recorded from the ear canal position (lower graphs) benchmarked against reference Lead I arm-ECGs (upper graphs).

FIG. 7 shows a high correspondence between the cardiac cycles recorded from the ear canals and the reference ECG (Lead I from the arms). Differences in the characteristic waveforms in the cardiac cycle in several recordings were correctly determined using the ear-ECG. Additionally, a ratio between an amplitude of the R-wave peak in Lead I and an R-wave peak in ear-ECG was approximately 50 across all subjects. There is generally good agreement between the reference ECG and ear-ECG data in that the P-, Q-, S-, and T-waves are detected at similar times with respect to the R-wave for both sets of data. Good agreement is achieved; typically to within 5 ms. For the ear canal data, the waves from 1) use R-wave timings obtained from the reference ECG from the arms (Lead I), and the waves from 2) use R-wave timings obtained from the individual head- and ear-ECG channels themselves, as discussed previously in Algorithm 1.

A comparison of the cardiac cycles of the ear-ECG and the reference Lead I ECG from the arms is provided below in Table 2 in terms of the: i) time difference between the cardiac features (the waves P-, Q-, R-, S- and T-waves in the cardiac cycle), ii) correlation of the cardiac cycles, iii) ratio between the amplitude of the waves and the amplitude of the R-wave in a given cycle, and iv) normalised variance. "Ref" denotes results for cardiac cycles for which the R-wave timings were obtained from the reference ECG (Lead I, on the arms), and "Sig" those for which the R-waves were obtained from the ear-ECG, a bipolar channel based on the potential across the head between two ears. The values represent the means across all five subjects and the first row displays the ideal values (the reference ECG compared to itself).

TABLE 2

Comparison of cardiac cycles from ear-ECG and conventional Lead I ECG

| Channel | i) Time difference | | ii) Correlation | | iii) Ampl. ratio | | iv) Var. |
|---|---|---|---|---|---|---|---|
| | Ref [ms] | Sig [ms] | Ref | Sig | Ref | Sig | |
| Reference | 0 | 0 | 1 | 1 | 1 | 1 | 0.22 |
| Ear canal | 8 | 9 | 0.96 | 0.90 | 1.57 | 1.43 | 2.31 |

Figure 8:
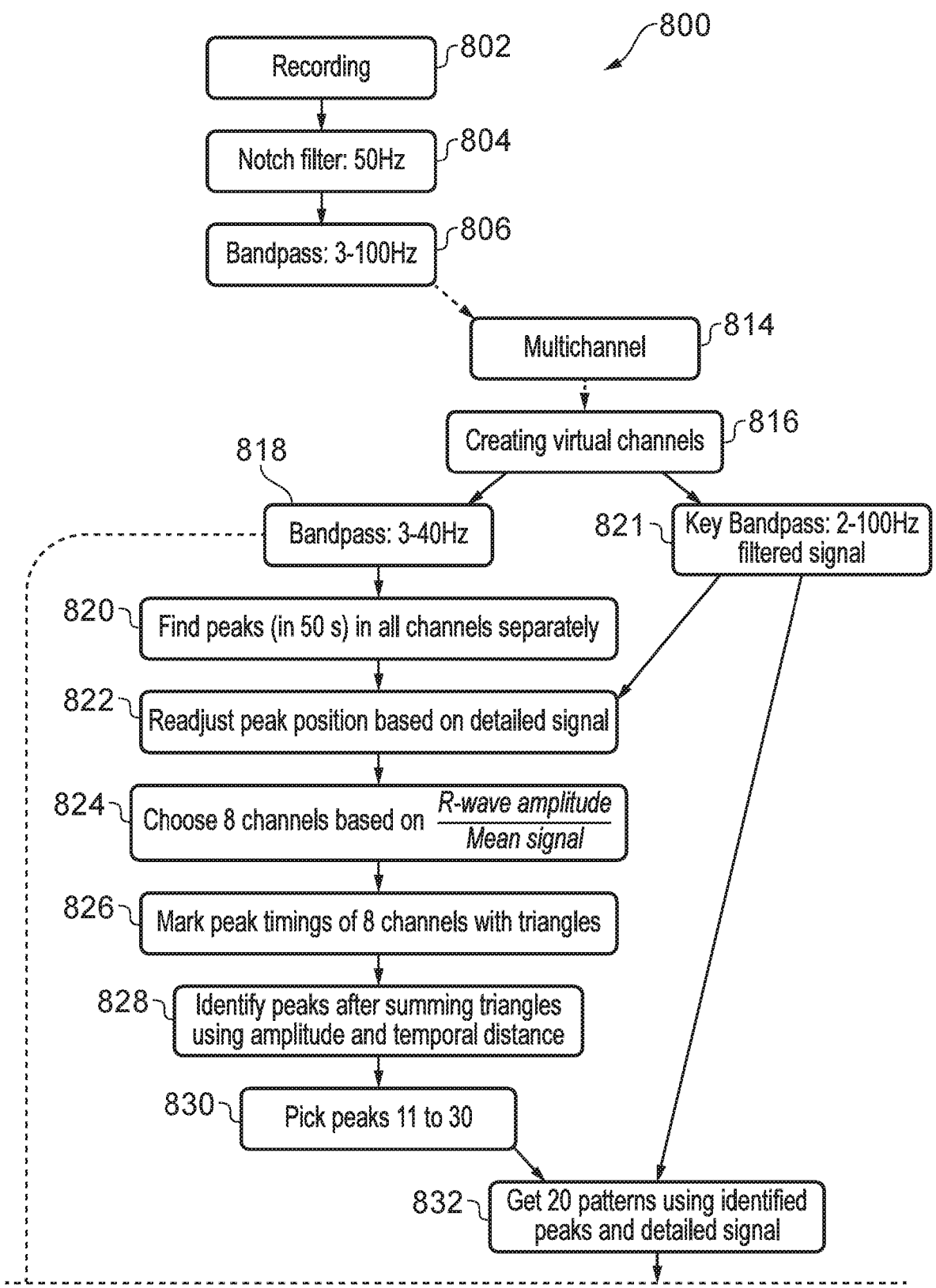
FIG. 8 illustrates an algorithm for identifying R-waves in a noisy electrocardiogram from multiple channels for a subject; and k.
Figure 8:
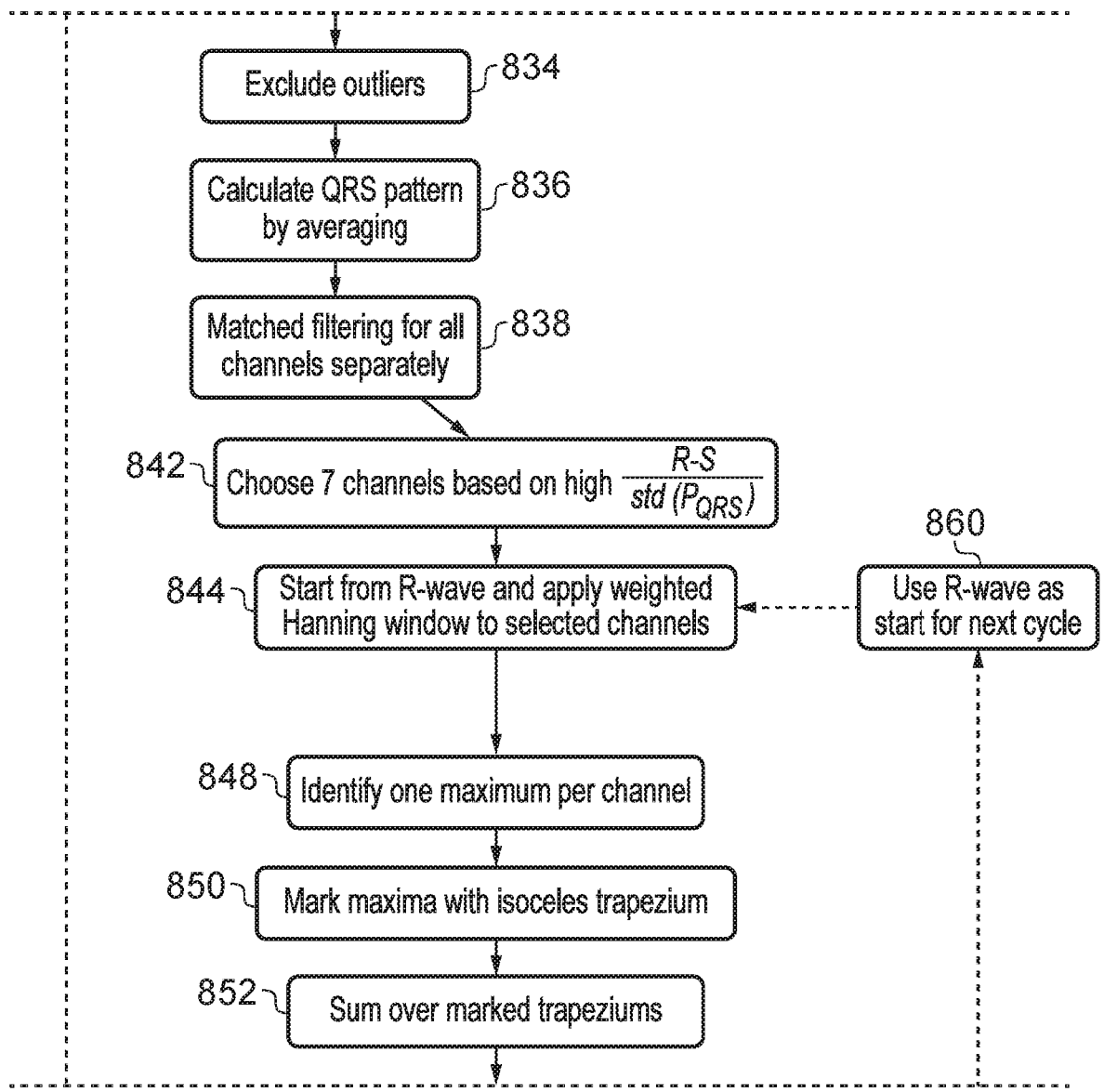
Figure 8:
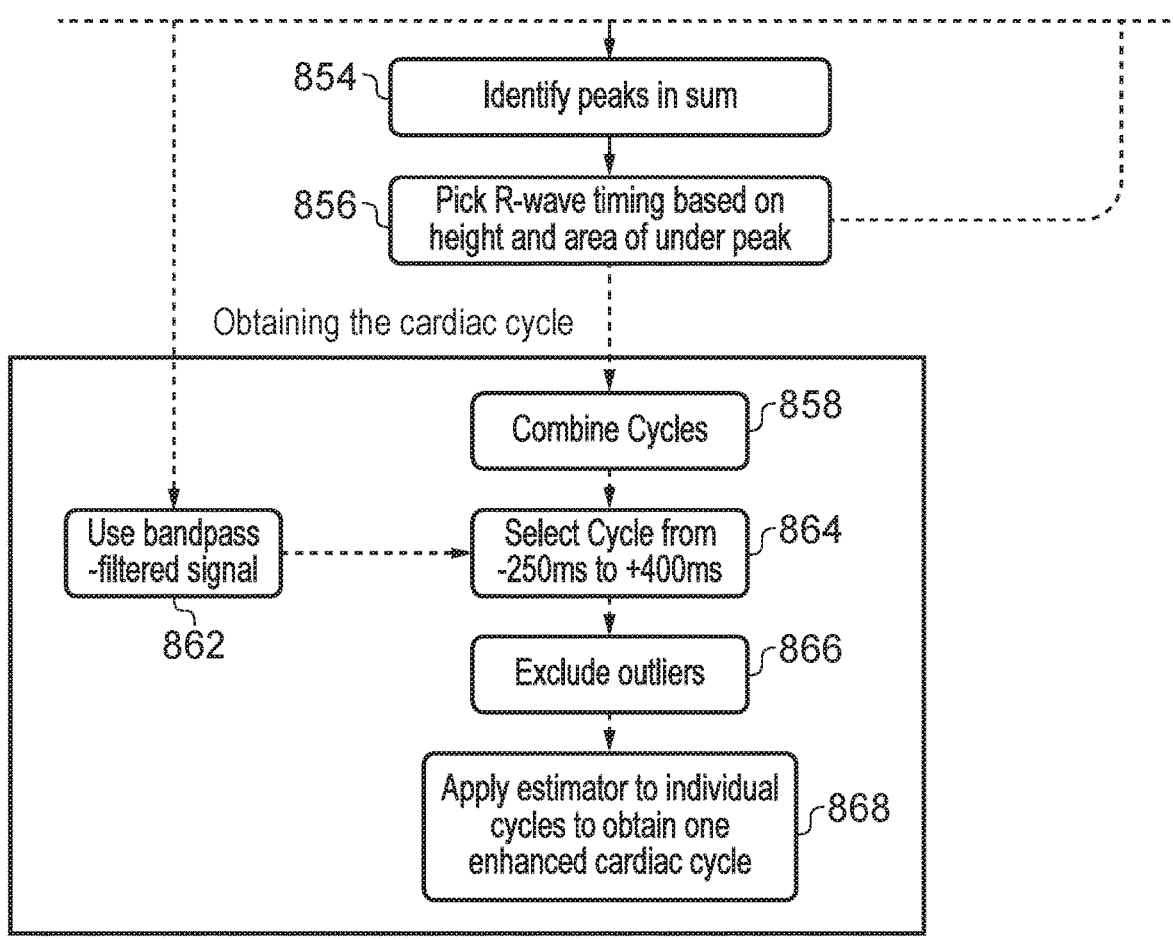

The provision of a full electrocardiogram (P-, Q-, R-, S-, T-waves) by the method of FIG. 3b, FIG. 8 or Algorithm 1 enables a disease of the subject to be diagnosed or a deviation from a normal cardiac state to be determined by comparing the obtained ECG with a typical cardiac cycle pattern for a known disease or condition. Such diagnosis may require a full ECG (including P-, Q-, R-, S-, T-waves, where available) and may not be obtainable using only the QRS component, in at least some cases. Such diagnosis may be used for curative purposes representing a deductive medical or veterinary decision phase, but is not a purely intellectual exercise when performed in the context of an automated method.

In some examples, one or more of the following additional (not necessarily sequential) steps may be performed:
1) Comparing the obtained ECG with patterns of known cardiovascular diseases.
2) Identifying indicators of irregularity in the ECG waveform (not necessarily including diagnosing a specific heart conditions, but deviations from a usual cardiac cycle; two examples are a deep Q-wave and an inverted T-wave).
3) Using a suitable signal processing algorithm or machine learning, or adaptive, algorithm to register a user's personal normal cardiac cycle and subsequently the identification of deviations from his/her own cardiac cycle. This includes person-specific variations, one example is the heart-rate dependent stretching or compression of the cardiac cycle.
4) Storing the ECG observed over time, or derived cardiac cycle, to enable a more meaningful analysis by a physician.
5) Transmitting the derived ECG to a physician or other user in case of abnormalities or an emergency.

The findings discussed with reference to FIGS. 5-7 demonstrate the ability of the head- and ear-based ECG set-ups to record cardiac cycles, the shapes of which are shown to be very similar to Lead I from the standard limb leads. The proposed head-ECG framework enables the examination of heart conditions that are visible in multiple consecutive cardiac cycles in Lead I. The following are examples of conditions or events that may be detectable using implementations of methods as described herein:
Myocardial infarction (reflected in an elevated ST segment),
First-degree atrioventricular block (the PR interval is longer than 200 ms),
Atrial fibrillation (the P-wave disappears, found in 2% to 3% of the population in Europe and the USA),
Sinus tachycardia (elevated regular heart rate, P-wave can be close to preceding T-wave),
Atrial flutter (atria contract at up to 300 bpm, atrioventricular node contracts at 180 bpm, frequency of P-waves is much higher than frequency of QRS-complexes),
General warning signs when something is unusual, e.g. departure from a subject's normal pattern.

More generally, the proposed methods and apparatus enable 24/7 continuous and unobtrusive cardiac monitoring and can alert the subject or another user, such as a clinician or physician, when a universal signature of heart malfunction, such as a deep Q-wave or an inverted T-wave, or another indicator of cardiac malfunction, are observed.

The device and method therefore open up a new perspective for numerous existing applications in the community, such as an insight into the activity of the autonomic nervous system (ANS) and its components, the parasympathetic nervous system (PNS) and sympathetic nervous system (SNS), and an early-warning and tele-monitoring system for certain cardiovascular diseases and/or human stress quantification.

FIG. 8 illustrates another example of a method 800 of obtaining an electrocardiogram for a subject. The method 800 relates to a more detailed example of the methods described previously with reference to FIG. 3b and Algorithm 1.

The method comprises receiving and recording electrical signals from at least two head mounted electrodes (box 802). The received signals are filtered (box 804) using a notch filter and subsequently a band pass filter (box 806). In this example, the notch filter (box 804) operates at a frequency of 50 Hz and the band pass filter (box 806) passes a band between 3-100 Hz.

FIG. 8 illustrates a multi-channel analysis process 814 for resolving shape and timing information for each of the P-, Q-, R-, S-, T-waves that are available for the subject over a number of cardiac cycles. The multi-channel process 814 involves creating virtual channels (box 816). Measurements may be obtained from duplicate sets of electrodes at a single pair of sites, for example multiple pairs of jaw-joints electrodes, to provide multiple sets of similar readings. It is assumed that the placement of the multiple pairs of electrodes are sufficiently close that the differences in readings between those pairs of electrodes are due to noise caused by the electrode-skin contacts. A virtual channel may be obtained by combining (for example, averaging and multiplying) the neighbouring channels to remove the noise from the signal.

The band pass filtered signals are further band passed in a first signal path at between 3-40 Hz (box 818) and in a second signal path the band passed signal (3-100 Hz) is kept (box 821). The band pass filtered signal from the first signal path is then subsequently analyzed to find R-peaks in all channels (box 820). In this example, the first 50 seconds of signal are assessed. The positions of the peaks are readjusted (box 822) based on a detailed signal using the band passed signal from the second signal path. Subsequently, a number of the virtual channels are chosen based on R-wave amplitude/mean signal amplitude (box 824). The peak signal timing is marked (box 826) in each of the chosen channels using a respective triangle, for example. The positions of the peaks are then identified (box 828) after summing the area of the triangles, in terms of amplitude and temporal distance, over the chosen number of channels. In this example, the 20 cycles per channel around the peaks 11-30 are then selected (box 830); the earlier peaks are ignored because they might typically include more noise than the later peaks. A number of cycles are obtained using the identified peaks and the detailed signal from the second path (box 832). Outlier values in the individual cycles are excluded (box 834) and one QRS pattern per channel is calculated by averaging over all of the cycles in this channel (box 836).

In one example pattern extraction (boxes 832, 834, 836), an average is taken over 20 cycles in the time domain. That means—before averaging—there are 20 values for every time point in the cardiac cycle. Out of those 20 values, 5% of the largest and smallest values, i.e. in this case the largest and the smallest, are rejected. Suitable alternatives with a similar outcome would be able to reject 10% on each side or using the median instead.

The 20 cycles in each channel are averaged to obtain one pattern per channel. (This is done to account for potential differences in the cardiac cycle between channels. For example, a channel with one electrode in the front and one in the back would look different from one between left and right.)

Matched filtering is performed for each of the channels separately (box 838). A number of the channels that have been subjected to match filtering (box 838) are chosen for subsequent processing. The chosen channels may be based on a comparison between (the mean R-wave amplitude—mean S-wave amplitude)/the standard deviation of the QRS pattern (box 842). All channels are taken into account simultaneously when identifying the R-wave of the QRS pattern. Starting from the detected R-wave, a Hanning window may be applied a number of times to the selected channels (box 844). One maximum is identified per channel (box 848) and the maximum is marked with an isosceles trapezium (box 850). The trapeziums are summed over all of the channels (box 852). The peaks in the summed values are identified (box 854) and R-wave timing is selected based on the height and area of each peak (box 856). At this point, a position of the R-wave in each channel has been identified. A combined cardiac cycle is generated (box 858) by performing the steps in boxes 864, 866, 868. The position of the R-wave may also be used to determine the start of the next cycle/channel (box 860). The band pass filtered signal from the first path is used (box 862) to select time periods for each cycle (box 864) based on the identified R-waves. Outliers are excluded (box 866) and an estimator is applied to individual cycles to obtain an enhanced cardiac cycle (box 868).

Figure 9:
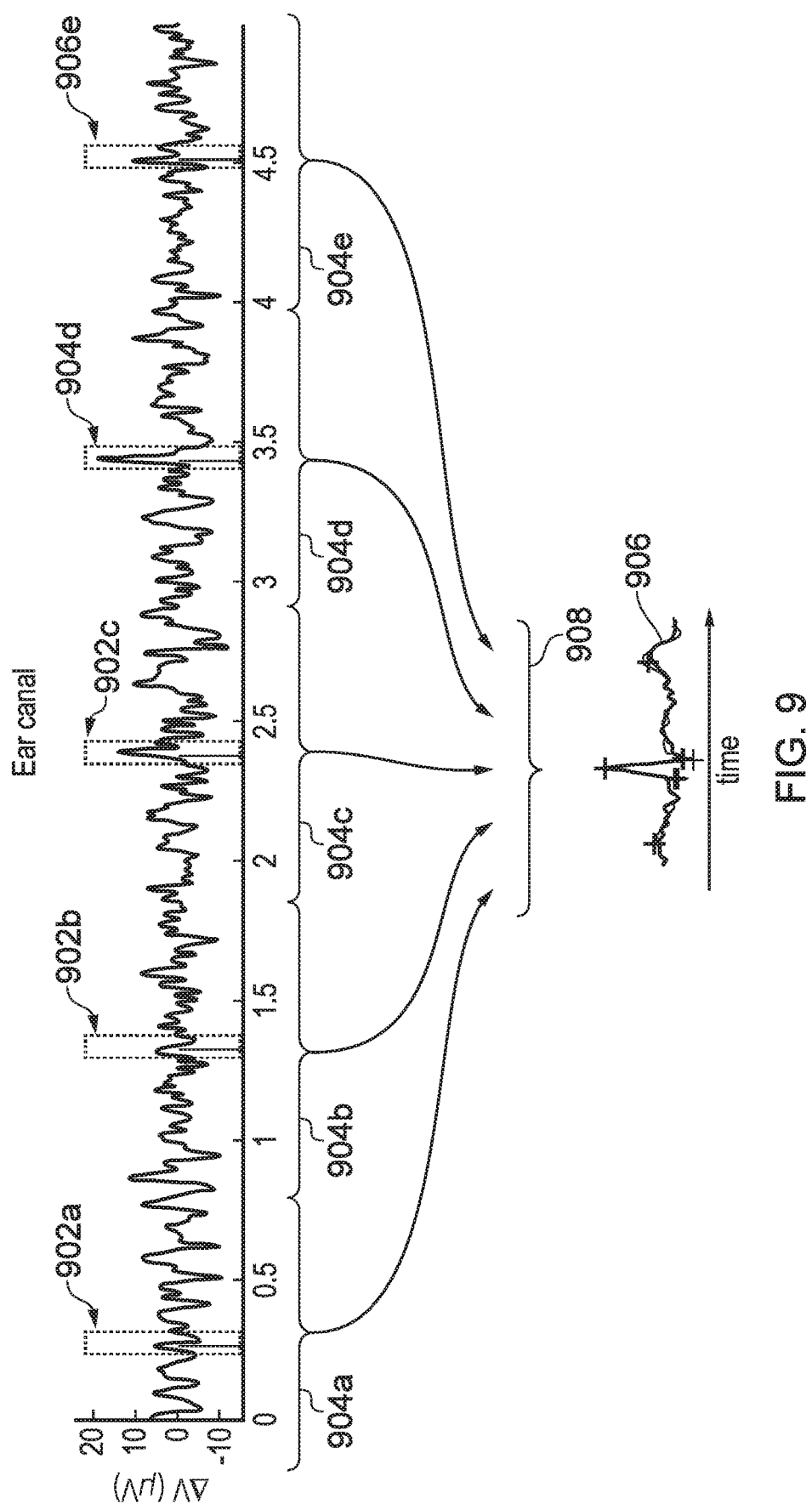
FIG. 9 demonstrates how plural cardiac cycles may be combined to provide a composite ECG.

FIG. 9 illustrates a schematic demonstrating how signals may be combined to derive an electrocardiogram 906 from head-mounted electrode data. The illustrated data are indicative only. A number of R-waves 902*a-e* are identified in a raw ECG obtained using a set of head electrodes. Each R-wave 902*a-e* is associated with a respective cardiac cycle period 904*a-e*. Each cardiac cycle period 904*a-e* is defined by a set of data samples. In practice, a cardiac cycle period may not be symmetrical around the R-wave and typically extends from 250 ms before the R-wave to 400 ms after the R-wave. The sets of data samples may be aligned based on the position of the R-wave 902*a-e* within each cardiac cycle period 904*a-e* to produce a combined waveform 906 for a single, composite electrocardiogram for a cardiac cycle period 908. The combined waveform 906 may be generated via a linear estimator (such as a weighted average or Kalman-filter) or a non-linear estimator/pattern recognition algorithm (such as neural network, Bayesian, robust statistics based algorithms) using each of the corresponding, aligned data samples within the sets of data samples and provides an electrocardiogram which resolves the combined shape and timing of any or all of the P-, Q-, R-, S-, T-waves available for the subject over the measurement period.

The electrocardiogram obtained may therefore be referred to as a composite electrocardiogram, that is, an electrocardiogram that comprises data combined over a number of cardiac cycles.

Other embodiments are intentionally within the scope of the accompanying claims.

The invention claimed is:

1. A method of obtaining an electrocardiogram for a subject, the method comprising:
receiving electrical signals from at least two sensors, the at least two sensors including at least two electrodes and the at least two electrodes comprising a plurality of pairs of electrodes, wherein receiving electrical signals from the at least two sensors comprises receiving electrical signals from the plurality of pairs of electrodes, each pair of electrodes defining a channel signal, in which all of the at least two electrodes are head-mounted electrodes; and
analyzing said electrical signals over a plurality of cardiac cycles to derive a composite electrocardiogram with shape and timing information for each of P-, Q-, R-, S- and T-waves available for the subject;
wherein analyzing said electrical signals comprises:
determining locations of R-waves in the electrical signals corresponding to plural cardiac cycles;
based on the R-wave locations, aligning multiple sets of data samples, each set of data samples corresponding to a cardiac cycle; and
combining the multiple data samples over the plural cardiac cycles to resolve any P-, Q-, S- and T-waves in the received electrical signals; and
wherein the at least two sensors include the at least two electrodes and at least one non-electrode sensor, wherein the at least one non-electrode sensor comprises at least one mechanical sensor, acoustic sensor or microphone, and a potential time window for the R-waves for each of the plurality of cardiac cycles is determined using a signal from the at least one non-electrode sensor,
wherein the method further comprises:
generating a plurality of virtual channels from the plurality of channel signals;
for each virtual channel of the plurality of virtual channels:
filtering the virtual channel through a first band pass filter to produce a first filtered signal,
filtering the virtual channel through a second band pass filter to produce a second filtered signal, wherein the first band pass filter has a narrower frequency range than the second band pass filter,
analyzing the first filtered signal to locate a plurality of R-wave peaks in the virtual channel, wherein the analysis is based on a detailed signal using the second filtered signal,
obtaining a plurality of cardiac cycles using the located plurality of R-wave peaks in the first virtual channel and the detailed signal from the second filtered signal,
averaging the plurality of cycles to obtain a QRS pattern for the virtual channel, and
identifying an R-wave position in the QRS pattern for the virtual channel;
generating a combined cardiac cycle for the plurality of virtual channels based on the identified R-wave positions; and
deriving the composite electrocardiogram from a plurality of cardiac cycles in the combined cardiac cycle, wherein the first filtered signal is used to select time periods for each cycle based on the identified R-wave positions.

2. The method of claim 1, in which the composite electrocardiogram is obtained using signals only from head-mounted sensors.

3. The method of claim 2 in which the received electrical signals include electrical signals from first and second head-mounted electrodes, and at least a third head-mounted electrode.

4. The method of claim 3 in which the third head-mounted electrode comprises an electrode disposed on a head in a position selected from the group consisting of: jaw, mastoid, concha, and forehead.

5. The method of claim 3 in which the received electrical signals further include electrical signals from the third head-mounted electrode disposed within a left ear or a right ear canal.

6. The method of claim 1 in which the received electrical signals from the at least two sensors derive from a left in-ear electrode and from a right in-ear electrode.

7. The method of claim 1 in which the at least two electrodes comprise electrodes that are disposed symmetrically on opposite sides of a sagittal plane to serve as a proxy for a body-mounted Lead I ECG electrode array.

8. The method of claim 1 in which the locations of R-waves in the electrical signals are at least partially determined by matching successive data samples against a predetermined template, by finding positions of maxima in the electrical signals, or based on the determined location of a previous R-wave.

9. The method of claim 1 in which a time difference between features in the electrocardiogram and the at least one non-electrode sensor are used to calculate the pulse wave velocity.

10. The method of claim 9 in which pulse wave velocity is used to calculate arterial stiffness.

11. The method of claim 1 in which the at least one non-electrode sensor is used to obtain a pulse waveform.

12. The method of claim 11 in which the pulse waveform is used to calculate arterial stiffness, blood pressure or other cardiovascular parameters.

13. The method of claim 1 in which cardiovascular parameters are calculated using a waveform of at least one signal modality and/or time differences between features in at least two modalities by applying deterministic or machine-learning techniques.

14. The method of claim 1, in which a signal from the at least one non-electrode sensor is used to denoise the measured electrocardiogram.

15. The method of claim 1, further comprising automatically comparing the composite electrocardiogram with one or more template patterns associated with one or more known cardiovascular states in order to determine whether the composite electrocardiogram corresponds to one of the known cardiovascular states.

16. The method of claim 15, in which the one or more known cardiovascular states comprise one or more known cardiovascular diseases or irregularities, or a healthy state.

17. The method of claim 1, further comprising:
applying an algorithm to register the subject's normal cardiac cycle; and
comparing the normal cardiac cycle with an electrocardiogram for a subsequent cycle in order to identify any deviations from the normal cardiac cycle.

18. The method of claim 1, in which the at least two electrodes comprise electrodes that are disposed on opposite sides of a coronal plane to serve as a proxy for front-to-back electrocardiogram.

19. The method of claim 1, wherein the at least two sensors comprise at least three sensors, and the at least three sensors include at least three electrodes, the method further comprising:
receiving electrical signals from the at least three sensors, the at least three sensors including at least three electrodes, in which all of the at least three electrodes are positioned on a head of the subject and define the plurality of pairs of electrodes, each pair of electrodes defining a channel signal.

20. The method of claim 19 in which all of the at least three electrodes are positioned in one or both ears of the subject.

21. The method of claim 1, in which the at least one non-electrode sensor is head mounted.

22. A processing module for obtaining an electrocardiogram of a subject, configured to:
receive electrical signals from at least two sensors, the at least two sensors including at least two electrodes and the at least two electrodes comprising a plurality of pairs of electrodes, wherein receiving electrical signals from the at least two sensors comprises receiving electrical signals from the plurality of pairs of electrodes, each pair of electrodes defining a channel signal, in which the at least two electrodes are all head-mounted electrodes; and
analyze said electrical signals to resolve shape and timing information for each of P-, Q-, R-, S- and T-waves available for the subject over a number of cardiac cycles, to derive a composite electrocardiogram;
wherein analyzing said electrical signals comprises:
determining locations of R-waves in the electrical signals corresponding to plural cardiac cycles;
based on the R-wave locations, aligning multiple sets of data samples, each set of data samples corresponding to a cardiac cycle; and
combining the multiple data samples over the plural cardiac cycles to resolve any P-, Q-, S- and T-waves in the received electrical signals;
wherein the at least two sensors include the at least two electrodes and at least one non-electrode sensor, wherein the at least one non-electrode sensor comprises at least one mechanical sensor, acoustic sensor or microphone, and a potential time window for the R-waves for each of the plurality of cardiac cycles is determined using a signal from the at least one non-electrode sensor; and
wherein the processing module is further configured to:
generate a plurality of virtual channels from the plurality of channel signals;
for each virtual channel of the plurality of virtual channels:
filter the virtual channel through a first band pass filter to produce a first filtered signal,
filter the virtual channel through a second band pass filter to produce a second filtered signal, wherein the first band pass filter has a narrower frequency range than the second band pass filter,
analyze the first filtered signal to locate a plurality of R-wave peaks in the virtual channel, wherein the analysis is based on a detailed signal using the second filtered signal,
obtain a plurality of cardiac cycles using the located plurality of R-wave peaks in the first virtual channel and the detailed signal from the second filtered signal,
average the plurality of cycles to obtain a QRS pattern for the virtual channel, and
identify an R-wave position in the QRS pattern for the virtual channel;
generate a combined cardiac cycle for the plurality of virtual channels based on the identified R-wave positions; and
derive the composite electrocardiogram from a plurality of cardiac cycles in the combined cardiac cycle, wherein the first filtered signal is used to select time periods for each cycle based on the identified R-wave positions.

\* \* \* \* \*